(12) United States Patent
Narayana et al.

(10) Patent No.: US 12,303,627 B2
(45) Date of Patent: May 20, 2025

(54) PERITONEAL DIALYSIS SYSTEM

(71) Applicant: MOZARC MEDICAL US LLC, Minneapolis, MN (US)

(72) Inventors: Rathnakara Narayana, Bangalore (IN); Rajkumar Vp, Dindigul (IN)

(73) Assignee: Mozarc Medical US LLC, Minneapolis, MN (US)

( * ) Notice: Subject to any disclaimer, the term of this patent is extended or adjusted under 35 U.S.C. 154(b) by 786 days.

(21) Appl. No.: 17/407,003

(22) Filed: Aug. 19, 2021

(65) Prior Publication Data

US 2023/0057660 A1     Feb. 23, 2023

(51) Int. Cl.
*A61M 1/28* (2006.01)
*A61M 1/14* (2006.01)
*A61M 39/10* (2006.01)
*A61M 39/16* (2006.01)

(52) U.S. Cl.
CPC ............ *A61M 1/28* (2013.01); *A61M 1/1524* (2022.05); *A61M 1/159* (2022.05); *A61M 39/1011* (2013.01); *A61M 39/16* (2013.01); *A61M 2205/12* (2013.01); *A61M 2205/121* (2013.01)

(58) Field of Classification Search
CPC ...... A61M 1/28; A61M 1/1524; A61M 1/159; A61M 2205/12; A61M 2205/121
See application file for complete search history.

(56) References Cited

U.S. PATENT DOCUMENTS 8,784,359 B2    7/2014  Plahey et al.
2007/0112297 A1*  5/2007  Plahey .................. A61M 1/155
                                                             604/28

OTHER PUBLICATIONS

U.S. Appl. No. 17/406,848, filed Aug. 19, 2021, naming inventors Vp et al.

\* cited by examiner

*Primary Examiner* — Bradley J Osinski

(57) ABSTRACT

An assembly includes first and second assemblies, the first assembly including a frame defining a recess, a first plate disposed within the recess, and a bellows disposed between the first plate and an inner surface of the frame. The second assembly includes a second plate configured to be opposite the first plate when the first assembly is in a closed position relative to the second assembly. The first assembly is configured to move relative to the second assembly between an open position and the closed position, and a latch assembly configured to hold the first assembly to the second assembly in the closed position. The bellows is configured to inflate to apply a force to the first plate towards the second plate when the first assembly is in the closed position.

17 Claims, 11 Drawing Sheets

PERITONEAL DIALYSIS SYSTEM

TECHNICAL FIELD

The present disclosure relates to peritoneal dialysis (PD) systems.

BACKGROUND

Peritoneal dialysis (PD) may be used to remove waste products from blood of a patient when the kidneys of the patient are no longer able to adequately do so. During PD, a PD cycler delivers a dialysate through a catheter into a peritoneal cavity of a patient. The peritoneum of the patient acts as a membrane through which waste products are removed from the blood of the patient via osmosis and diffusion. Waste products and fluid pass from the blood of the patient, through the peritoneum, and into the dialysate. After a dwell period, the PD cycler removes an effluent fluid from the peritoneal cavity, which includes the dialysate and filtered waste products, from the patient's peritoneal cavity through the catheter.

SUMMARY

This disclosure describes example devices, systems, and techniques related to PD systems, including devices, systems, and techniques related to connecting PD cassettes with PD devices (also referred to herein as PD cyclers). APD cassette may be used as a disposable component of a PD system that defines a plurality of fluid flow paths between inputs and outputs of a fluid circuit including the peritoneal cavity of the patient. Physical/mechanical components of the PD device may interact with the PD cassette to affect the fluid flow through the fluid circuit without physically contacting the fluid, thereby maintaining the sterility of the fluid and the fluid circuit. The cassette and connecting lines may be disposable and used once or a few times over a relatively short period of time, and replaced with a new, sterile cassette and connecting lines for subsequent therapy.

The PD device may use the PD cassette as a fluid switch to select between the multiple inputs and outputs of the fluid circuit including the patient and the cassette, e.g., inputs/outputs such as PD bags including dialysate, dialysate conditioners such as heater bags, waste lines, and fluid lines connected to a catheter disposed within the peritoneal cavity of the patient. The cassette includes a membrane and housing that define the plurality of flow paths. The PD device may be configured to receive and hold the cassette and provide a pressure to the membrane to seal the membrane to the cassette housing. The cassette housing may define a plurality of channels corresponding to the flow paths, and the flow paths may be formed via sealing of the membrane to the housing which seals each channel. The PD device may select a particular flow path connecting an input and an output within the cassette by occluding/stopping some flow paths within the cassette while leaving other flow paths unoccluded/open for fluid flow. The PD device may occlude/stop a fluid flow path by applying a localized pressure to the membrane via an actuator configured to depress the membrane within a channel of the cassette housing and thereby occluding/stopping the flow of fluid through that channel.

In examples described herein, a PD cassette mounting assembly is configured to hold and align a PD cassette with a PD device in order to fluidically connect one or more fluid inputs and outputs of the PD device via the cassette. The PD cassette mounting assembly is also configured to apply pressure to a cassette membrane and to create a seal with the membrane to form one or more fluid flow paths within the cassette. The PD cassette mounting assembly is also configured to mechanically lock the PD cassette mounting assembly in a closed position during application of pressure to the cassette, e.g., to prevent the PD cassette mounting assembly from being opened while pressure is being applied.

Clause 1. An assembly comprising: a first assembly comprising: a frame defining a recess; a first plate disposed within the recess; and a bellows disposed between the first plate and an inner surface of the frame; a second assembly comprising a second plate configured to be opposite the first plate when the first assembly is in a closed position relative to the second assembly, wherein the first assembly is configured to move relative to the second assembly between an open position and the closed position; and a latch assembly configured to hold the first assembly to the second assembly in the closed position, wherein the bellows is configured to inflate to apply a force to the first plate towards the second plate when the first assembly is in the closed position.

Clause 2. The assembly of clause 1, wherein the assembly is configured to receive a cassette when the first assembly is in the open position.

Clause 3. The assembly of clause 1 or clause 2, wherein the first assembly further comprises a first gasket disposed on the first plate between the first plate and the second plate, and wherein the second assembly further comprises a second gasket disposed on the second plate between the second plate and the first plate.

Clause 4. The assembly of clause 3, wherein the assembly is configured to receive a cassette when the first assembly is in the open position, and wherein the assembly is configured to hold the cassette between the first gasket and the second gasket when the first assembly is in the closed position.

Clause 5. The assembly of any one of clauses 1 through 4, wherein the latch assembly is configured to lock the first assembly in the closed position when the bellows applies the force to the first plate.

Clause 6. The assembly of clause 5, further comprising a latch bar attached to the second assembly, wherein the latch assembly further comprises: first and second jaws configured to receive the latch bar when the first and second jaws are open, wherein the first and second jaws are configured to close and hold the latch bar when the first and second jaws are latched closed, wherein the latch assembly is configured to hold the first assembly to the second assembly in the closed position when the first and second jaws are latched closed and holding the latch bar; and an actuator configured to extend a pin configured to mechanically engage and prevent the first and second jaws from opening from being latched closed while the bellows apply the force to the first plate, wherein the actuator is configured to retract the pin to enable the first and second jaws to open while the bellows are not applying the force to the first plate.

Clause 7. The assembly of clause 6, wherein the actuator is a pneumatic actuator pneumatically connected to a compressor, wherein the bellows are pneumatically connected to the compressor, and wherein the actuator is configured to extend the pin when the compressor provides air to the bellows.

Clause 8. The assembly of any one of clauses 1 through 7, wherein the assembly is configured to hold a cassette between the first plate and the second plate when the first assembly is in the closed position, the cassette comprising a cassette membrane and a cassette housing, and wherein when the cassette is positioned between the first plate and the second plate and the first assembly is in the closed position, the force is sufficient to cause the first plate to apply a pressure to seal the cassette membrane to the cassette housing and selectively block one or more fluid flow paths within the cassette.

Clause 9. The assembly of clause 8, wherein the second plate is configured to hold a linear actuator in a position such that the linear actuator, when activated, changes at least one fluid flow path of the one or more fluid flow paths within the cassette, wherein the second plate is configured to hold a sensor configured to sense a parameter of a fluid within the cassette.

Clause 10. The assembly of any one of clauses 2 through 9, further comprising the cassette.

Clause 11. A peritoneal dialysis cassette mounting assembly comprising: a first plate; a second plate opposing the first plate and separate from the first plate by a predetermined distance, wherein the first plate is configured to move towards or away from the second plate; and a bellows disposed opposite the first plate from the second plate and configured to apply a force to the first plate towards the second plate upon inflation.

Clause 12. The peritoneal dialysis cassette mounting assembly of clause 11 further comprising: a first assembly comprising a frame configured to hold the first plate; and a second assembly comprising a frame configured to hold the second plate, wherein the first assembly is configured to move relative to the second assembly between an open position and a closed position.

Clause 13. The peritoneal dialysis cassette mounting assembly of clause 12 further comprising: a latch assembly configured to hold the first assembly to the second assembly in the closed position and to lock the first assembly in the closed position when the bellows applies the force to the first plate.

Clause 14. The peritoneal dialysis cassette mounting assembly of clause 13 further comprising a latch bar attached to the second assembly, wherein the latch assembly further comprises: first and second jaws configured to receive the latch bar when the first and second jaws are open, wherein the first and second jaws are configured to close and hold the latch bar when the first and second jaws are latched closed, wherein the latch assembly is configured to hold the first assembly to the second assembly in the closed position when the first and second jaws are latched closed and holding the latch bar; and an actuator configured to extend a pin configured to mechanically engage and prevent the first and second jaws from opening from being latched closed while the bellows apply the force to the first plate, wherein the actuator is configured to retract the pin to enable the first and second jaws to open while the bellows are not applying the force to the first plate.

Clause 15. The peritoneal dialysis cassette mounting assembly of clause 14, wherein the actuator includes a pneumatic actuator pneumatically connected to a compressor, wherein the bellows are pneumatically connected to the compressor, and wherein the actuator is configured to extend the pin when the compressor provides air to the bellows.

Clause 16. The peritoneal dialysis cassette mounting assembly of any one of clauses 12 through 15, wherein the peritoneal dialysis cassette mounting assembly is configured to hold a cassette between the first plate and the second plate when the first assembly is in the closed position, the cassette comprising a cassette membrane and a cassette housing, and wherein when the cassette is positioned between the first plate and the second plate and the first assembly is in the closed position, the force is sufficient to cause the first plate to apply a pressure to seal the cassette membrane to the cassette housing and define one or more fluid flow paths within the cassette.

Clause 17. The peritoneal dialysis cassette mounting assembly of claim 16, wherein the second plate is configured to hold a linear actuator in a position such that the linear actuator, when activated, changes at least one fluid flow path of the one or more fluid flow paths within the cassette, wherein the second plate is configured to hold a sensor configured to sense a parameter of a fluid within the cassette.

Clause 18. The peritoneal dialysis cassette mounting assembly of clause 16, further comprising the cassette.

Clause 19. A method comprising: placing a peritoneal dialysis cassette in a peritoneal dialysis cassette mounting assembly, the peritoneal dialysis cassette mounting assembly comprising: a door assembly comprising: a frame defining a recess; first plate disposed within the recess; and a bellows disposed between the first plate and an inner surface of the frame; a fixed plate assembly comprising a second plate configured to be opposite the first plate when the door assembly is in a closed position relative to the fixed plate assembly, wherein the door assembly is configured to move relative to the fixed plate assembly between an open position and the closed position; and a latch assembly configured to hold the door assembly the fixed plate assembly in the closed position, wherein the peritoneal dialysis cassette is placed between the first plate and the second plate when the door assembly is in the closed position, wherein the bellows is configured to inflate to apply a force to the first plate towards the second plate when the door assembly is in the closed position; latching, via the latch assembly, the door assembly; and causing the bellows to inflate to cause the bellows to apply a force to the first plate towards the second plate upon inflation and when the first assembly is in the closed position, wherein the force causes the first and second plates to apply a pressure to seal a cassette membrane to the cassette and define one or more fluid flow paths within the cassette.

Clause 20. The method of clause 19, further comprising locking, via an actuator, latch assembly in a latched position upon inflating the bellows with the door assembly in the closed position.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
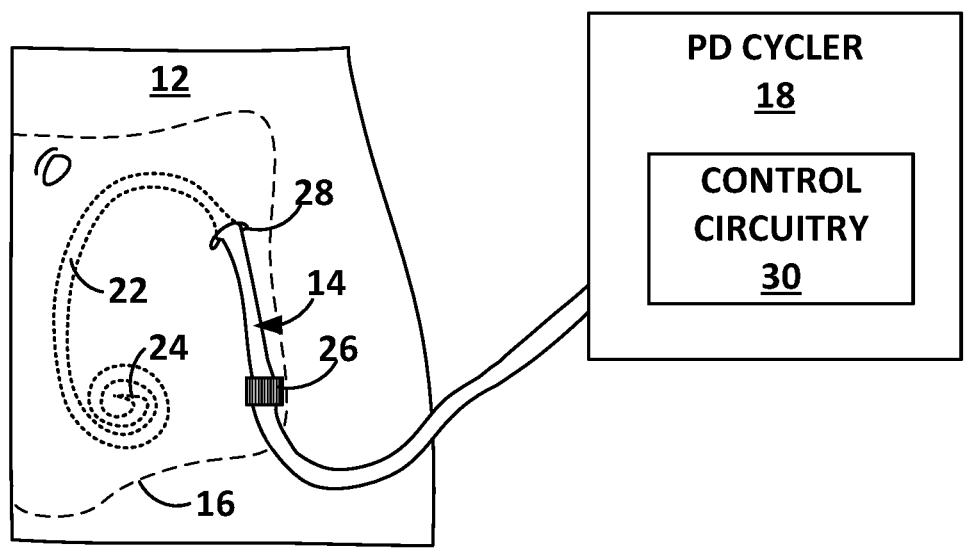
FIG. 1 is a diagram illustrating an example PD system configured to provide a patient with PD treatment.

This disclosure describes example devices, systems, and techniques for connecting peritoneal dialysis (PD) cassettes with PD devices, which are primarily referred to here as PD cyclers. In examples described herein, a PD cassette mounting assembly is configured to hold and align a PD cassette in order to fluidically connect one or more fluid inputs of the PD system with one or more fluid outputs of the PD system via the cassette. The PD cassette mounting assembly is also configured to apply pressure to a cassette membrane of the PD cassette to create a seal with the membrane forming one or more fluid flow paths within the cassette. The PD cassette mounting assembly is also configured to mechanically lock the PD cassette mounting assembly in a closed position during application of pressure to the cassette, e.g., to prevent the PD cassette mounting assembly from being opened while pressure is being applied.

Automated peritoneal dialysis (APD) uses a machine, called a cycler or a PD cycler, to automatically infuse, dwell, and drain peritoneal dialysis solution to and from a patient's peritoneal cavity. APD may be performed at night while the patient is asleep. An APD sequence typically lasts for several hours and may begin with an initial drain cycle to empty the peritoneal cavity of spent dialysate. The APD sequence then proceeds through a succession of fill, dwell, and drain phases occurring in sequential order. Each fill/dwell/drain sequence may be referred to as a PD cycle. During the fill phase, the PD cycler transfers a predetermined volume of fresh, warmed dialysate into the peritoneal cavity of the patient. The dialysate remains (or "dwells") within the peritoneal cavity for a time during the dwell phase. During the drain phase, the PD cycler removes the dialysate and waste (together referred to as effluent fluid) from the peritoneal cavity of the patient. The number of fill/dwell/drain cycles that are required during a given APD session depends upon the total volume of dialysate prescribed for the patient.

The PD cycler transfers fluids between the peritoneal cavity of the patient and a plurality of inputs and outputs, such as by selectively fluidically connecting one or more inputs with one or more specific outputs to create a desired fluid flow path through the PD system. For example, the inputs and outputs may be one or more fresh bags of PD dialysate, a heater bag and/or fluid heating apparatus, the peritoneal cavity of the patient, or waste bags. The PD cycler may be configured to cause fluid to move, e.g., via a pumping mechanism, through tubing fluidically connected to the cassette. The cassette defines a plurality of fluid pathways (also referred to herein as fluid flow paths or flow paths) configured to fluidically interconnect the various inputs and outputs. In some examples, the cassette may include the pumping mechanism, e.g., one or more diaphragms. In these examples, the PD cycler may be configured to move a membrane of the diaphragm to move and cause a pressure differential, causing fluid to move through a fluid circuit defined at least in part by the cassette.

In some examples, the inputs, outputs, tubing, and cassette connecting the inputs and outputs are fluidically separated from the PD cycler. For example, the tubing and the cassette may be disposable, and the PD cycler may be isolated from any fluids to maintain sterility of the fluids. In some examples, the PD cycler includes an air compressor configured to cause a pumping mechanism, e.g., either a diaphragm pump of the cassette or any other suitable pumping mechanism, to operate to move fluid and one or more actuators configured to engage with the cassette and select between one or more fluid pathways defined at least in part by the cassette. For example, the actuators can physically engage with certain parts of the cassette to selectively cause fluid to flow through one or more specific fluid pathways defined at least in part by the cassette and not flow through other one or more fluid pathways. The use of such a cassette may eliminate the need for directional control valves, which may simplify the PD cycler.

For example, the cassette may include a flexible membrane disposed over a plurality of channels defined by a housing of the cassette. The one or more actuators of the PD cycler may be configured to depress the flexible membrane at one or more positions in the channels of the cassette thereby blocking the fluid channel. Other channels may be left open, and the PD cycler may select between a plurality of pathways between the various inputs and outputs by closing/opening certain channels in the cassette. In this way, no portion of the PD cycler may come into contact with the fluid, thereby maintaining the sterility of the fluids between the inputs, outputs, and peritoneal cavity of the patient.

In some examples, a pressure is applied to the membrane of a cassette in order for the cassette to define the one or more flow paths. For example, a rigid housing of the cassette may include a plurality of recessed channels, and a particular flow path of a plurality of available flow paths may be defined by pressing a membrane to one or more surfaces of the housing such that the recessed channels are sealed by the membrane to form the one or more fluid pathways of the cassette. A PD cycler may include a cassette assembly in which the cassette is placed in the assembly with one or more channels aligned with one or more actuators configured to depress at least a portion of the membrane into one or more channels (or otherwise against a rigid surface) to block one or more fluid pathways, and the assembly may be configured to simultaneously apply a pressure to the membrane (e.g., via a support plate and a face plate) to seal the channels. However, if the pressure is released during filling/draining, fluid may leak from one fluid pathway to another within the cassette, the cassette diaphragm pump may not be able to provide a pressure differential to move fluid, or both. For example, if the cassette mounting assembly is opened during a fill/drain phase of a cycle, PD dialysate may leak into a fluid pathway bypassing the patient and directly into a waste bag, or fluid from the patient including waste may leak into fresh PD dialysate bags or back into the peritoneum of the patient.

According to examples disclosed herein, a PD cassette mounting assembly is configured to hold and align a PD cassette to a PD cycler. The PD cassette mounting assembly is also configured to apply pressure to a cassette membrane to create a seal with the membrane forming one or more fluid paths within the cassette and to fluidically connect one or more fluid inputs and outputs via the cassette. The PD cassette mounting assembly is configured to selectively apply pressure to a plurality of different parts of the cassette membrane to create a plurality of fluid paths within the cassette. The PD cassette mounting assembly is also configured to mechanically lock the PD cassette mounting assembly in a closed position during application of pressure to the cassette, e.g., to prevent the PD cassette mounting assembly from being opened during a fill/drain phase of a PD cycle and while pressure is being applied to the cassette.

The PD cassette mounting assembly described herein may improve the delivery of PD therapy and the sterility of the PD cycler system, and the fluids delivered to a patient, by at least preventing leaking of fluids between fluid flow paths in the PD system. For example, the PD cassette mounting assembly helps prevents opening of the cassette mounting assembly while fluids are flowing within the PD cassette thereby preventing inadvertent leaking of PD dialysate and/or effluent.

FIG. 1 is a diagram illustrating an example PD system 10 configured to provide patient 12 with PD treatment. PD system 10 includes a catheter 14, which is illustrated as extending into a peritoneal cavity 16 of patient 12, a PD cycler 18, and control circuitry 30.

PD cycler 18 is configured to deliver a dialysate into peritoneal cavity 16 via catheter 14. The dialysate remains in peritoneal cavity 16 for a dwell period, which has a duration that is intended to, but may not always be, sufficient for the exchange of waste products across a peritoneum of patient 12 to take place. In some such examples, PD cycler 18 may be disconnected from catheter 14 during the dwell period. In other examples, however, PD cycler 18 remains connected to catheter 14 during the dwell period. After the dwell period, PD cycler 18 removes fluid from peritoneal cavity 16. The fluid drained from peritoneal cavity 16 can be referred to as an effluent fluid, which contains the dialysate and the waste products removed from the blood of patient 12. In some examples, PD cycler 18 may be an active cycler configured to move fluid via a pump. In other examples, PD cycler 18 may be a passive cycler configured to move fluid via gravity.

Waste products may be removed from the bloodstream of patient 12 by the dialysate via an osmosis, e.g., a concentration gradient of an osmotic agent across the peritoneum of patient 12. A higher concentration of the osmotic agent created in peritoneal cavity 16 by filling peritoneal cavity 16 with dialysate including a concentration of the osmotic agent drives ultrafiltration and convective solute removal. The dialysate may include water, and dextrose or other sugars, salt, electrolytes, ions, amino acids, glucose polymers, and/or minerals as the osmotic agent. In some examples, the dialysate is dextrose-based, e.g., includes dextrose as the osmotic agent. Examples of dextrose-based dialysates include, but are not limited to, Dianeal available from Baxter Healthcare Corporation of Deerfield, IL and Delflex® available from Fresenius Medical Care of Waltham, MA In other examples, the dialysate may be characterized in having relatively low amounts of glucose degradation products (GDPs) and/or having a neutral pH (e.g., a pH of or close to 7). Examples of such dialysates include, but are not limited to, Physioneal available from Baxter Healthcare Corporation of Deer Field, IL, balance available from Fresenius Medical Care of Waltham, MA, and bicaVera® available from Fresenius Medical Care of Waltham, MA In yet other examples, dialysates may be icodextrin-based, such as Extraneal available from Baxter Healthcare Corporation of Deer Field, IL, or amino acid-based, such as Nutrineal™ available from Baxter Healthcare Corporation of Deer Field, IL.

In order to deliver the dialysate into peritoneal cavity 16 and remove the effluent fluid from peritoneal cavity 16, PD cycler 18 is connected to catheter 14, such as via an adapter 26, which provides the necessary mechanical connection between catheter 14 and PD cycler 18 to establish fluid communication therebetween. Catheter 14 may be any fluid delivery conduit capable of being inserted into peritoneal cavity 16 and connected to PD cycler 18 to facilitate PD treatment of patient 12. Catheter 14 defines an inner lumen 22 through which fluid may flow from PD cycler 18 to peritoneal cavity 16 and from peritoneal cavity 16 to PD cycler 18. Inner lumen 22 terminates at a distal opening, which can be at a distal-most end 24 of catheter 14, as shown in FIG. 1, and/or along a sidewall proximal to the distal-most end of catheter 14. Catheter 14 may be inserted into patient 12 via an exit site 28, and be configured to remain in patient 12 on a long-term basis.

Catheter 14 can have any suitable configuration. For example, the portion of catheter 14 that remains within peritoneal cavity 16 may be straight or curvilinear, such as coiled (e.g., pig-tailed) as shown in FIG. 1. In some examples, a distal portion of catheter 14 has a swan neck (e.g., a curved portion 40, shown in FIGS. 2 and 3, curved up to about 180 degrees), which may help position catheter 14 at exit site 28 as intended. Catheter 14 has any suitable length for accommodating PD treatment. For example, catheter 14 may be between about 57 cm and about 62 cm in length (e.g., from adapter 26 to a distal-most end of catheter 14 within peritoneal cavity 16), and may be between about 2.5 mm and about 3.5 mm in diameter. In other examples, other shapes, sizes (e.g., length or diameter), and/or configurations may be used. An example of catheter 14 includes, but is not limited to, the Argyle™ Peritoneal Dialysis Catheter available from Medtronic, Inc. of Minneapolis, MN.

In order to deliver the dialysate into peritoneal cavity 16 and remove the effluent fluid from peritoneal cavity 16, PD cycler 18 is configured to house and interact with a PD cassette. PD cycler 18 includes assemblies configured to hold the cassette, apply pressure to a cassette membrane of the PD cassette to seal the membrane to the cassette and define fluid flow paths (e.g., by closing one or more fluid flow paths to cause fluid to flow through one or more open fluid flow paths) within the cassette, and assemblies to hold actuators to apply localized pressure to select and deselect flow paths within the cassette.

In examples described herein, PD cycler 18 is configured to hold the PD cassette using a fixed plate assembly and a door assembly configured to move relative to the fixed plate assembly between an open position and a closed position. The fixed plate assembly includes a first plate (also referred to herein as a fixed plate) and the door assembly includes a second plate (also referred to herein as an opposing plate). When the door assembly is in a closed position relative to the fixed plate assembly, the fixed plate and the opposing plate are opposite each other and are configured to move towards or away from each other, e.g., such as by movement of the opposite plate towards or away from the fixed plate, respectively. For example, the PD cycler 18 may further include a bellows, or a plurality of bellows, configured to apply a force to the opposing plate towards the fixed plate upon inflation of the bellows. A PD cassette may be placed between the two plates and PD cycler 18 may apply a pressure to the cassette membrane via inflation of the bellows causing the opposing plate to press towards the fixed plate.

In some examples, the opposing plate may be disposed within a recess defined at least in part by a frame, such as a door frame configured to pivot (e.g., swivel) between and open position and a closed position relative to a device frame of PD cycler 18. The bellows may be disposed between the opposing plate and an inner surface of the door frame, e.g., so as to apply a force to the opposing plate away from the inner surface of the door frame. The fixed plate may be mounted to the frame of PD cycler 18 such that it opposes the opposing plate with the door is in the closed position. A device frame of PD cycler 18 can be any suitable structure of PD cycler 18 and, in some examples, may be part of a housing of PD cycler 18, a chassis of PD cycler 18, or the like.

PD cycler 18 may further include a latch assembly to hold the door frame to the PD cycler 18 frame in the closed position. The latch assembly may be further configured to lock, thereby holding or locking the door frame in the closed position, e.g., while the bellows applies the force to the opposing plate. For example, a pneumatic actuator may be pneumatically connected to a compressor configured to inflate the bellows such that the actuator extends a pin when the compressor provides air to the bellows. The pin may be configured to mechanically engage components of the latch to prevent the latch from opening while the bellows are inflated and applying a force to the opposing plate. This may help prevent inadvertent opening of the door during a dialysis session, which may help prevent unintended leakage of fluid from PD system 10.

In the example shown, PD cycler 18 includes control circuitry 30. Control circuitry 30 is configured to control PD cycler 18 to deliver PD therapy to patient 12 during a PD cycle. For example, control circuitry 30 may cause PD cycler 18 to deliver a dialysate into peritoneal cavity 16 via catheter 14 and may cause PD cycler 18 to remove fluid from peritoneal cavity 16 via catheter 14, e.g., after a dwell time.

For example, control circuitry 30 may be configured to cause an air compressor to provide pneumatic pressure to the bellows, one or more pneumatic actuators configured to engage with a cassette to change at least one fluid flow path of the one or more fluid flow paths defined by channels within the cassette, and a pneumatic locking actuator including a pin configured to engage the latch assembly to lock the latch. For example, a user may mount a cassette on the fixed plate, or adjacent to a gasket on the fixed plate, close the door frame (also referred to herein generally as a door) pivotably mounted to the device frame of PD cycler 18, latch the door in the closed position via the latch, and initiate a PD therapy treatment via a user interface of PD cycler 18. In response to the initiation of PD therapy treatment by the user, control circuitry 30 may cause an air compressor to provide air to one or more pneumatic actuators that are configured to, in response to receiving the air, extend a pin physically blocking the latch mechanism from opening. The air compressor is also configured to also provide air to the bellows to inflate and force the opposing plate within the door to compress the cassette, or a gasket of the opposing plate to compress the cassette.

During one or more stages of PD therapy, control circuitry 30 causes air to be selectively provided to one or more pneumatic actuators to locally depress the membrane of the cassette to occlude one or more particular channels, thereby selecting a fluid flow path for the stage of PD therapy, e.g., providing PD fluid to a heater bag, providing PD fluid to the patient, removing effluent from the patient, or the like. After PD therapy, control circuitry 30 may cause the compressor or another component to reduce the air and/or air pressure provided to the bellows and the pneumatic actuator locking the latch. The bellows may deflate, and a component providing a force in the direction opposite the force provided by the bellows, e.g., one or more springs, may cause the opposing plate to reduce the pressure applied to the cassette and/or move away from the cassette. In response to the reduction in the air pressure, the pin may retract, enabling a user to open the swiveling door to remove the cassette and, in some examples, change the cassette for a subsequent PD therapy session.

Control circuitry 30, as well as other processors, processing circuitry, controllers, control circuitry, and the like, described herein, may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, control circuitry 30 may include multiple components, such as any combination of one or more microprocessors, one or more DSPs, one or more ASICs, or one or more FPGAs, as well as other discrete or integrated logic circuitry, and/or analog circuitry. The functions attributed to control circuitry 30, as well as other processors described herein, may be embodied as firmware, hardware, software or any combination thereof.

In some examples, control circuitry 30 can be part of PD cycler 18, while in other examples, control circuitry 30 can be part of a different device, such as a clinician computer that is located near PD cycler 18 or remotely located (e.g., more than 50 feet away) from PD cycler 18. Although not shown in FIG. 1, control circuitry 30 may be part of a device that includes additional components, such as, but not limited to, a memory, a telemetry module that includes circuitry to facilitate communication between control circuitry 30 and another component, such as a power source.

PD cycler 18 and control circuitry 30, when control circuitry 30 is a part of a different device, are configured to communicate with each other using any suitable communication technique and via any suitable wired or wireless communication channels. Control circuitry 30 and PD cycler 18 may communicate via any of a variety of local wireless communication techniques, such as radio frequency (RF) communication according to the 802.11 or Bluetooth® specification sets, infrared (IR) communication according to the IRDA specification set, or other standard or proprietary telemetry protocols, or via remote telemetry such as, for example, via a local area network (LAN), wide area network (WAN), public switched telephone network (PSTN), or cellular telephone network.

Control circuitry 30 may also communicate with another computing device via a wired or wireless connection using any of any of the local or remote wireless communication techniques discussed with respect to communication between PD cycler 18 and control circuitry 30. Control circuitry 30 may also communicate with other computing devices via exchange of removable media, such as magnetic or optical disks, memory cards, or memory sticks.

Figure 2:
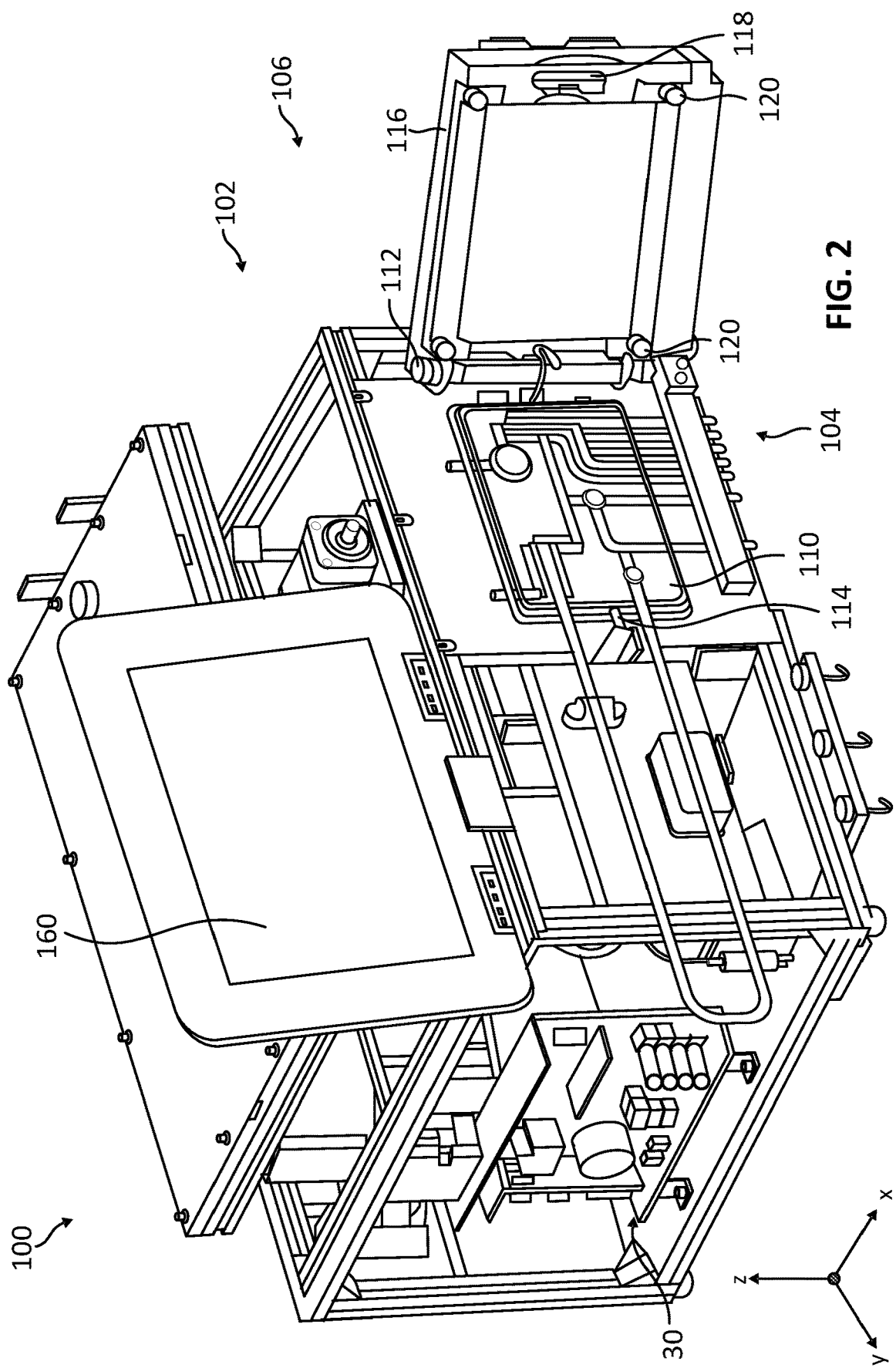
FIG. 2 is a perspective view of an example PD cycler with a PD cassette assembly in a closed position.

FIG. 2 is a perspective view of an example PD cycler 100 with a PD cassette assembly 102 in an open position. PD cassette assembly 102 includes fixed plate assembly 104 and door assembly 106 (e.g., a movable plate assembly). PD cycler 100 is an example of PD cycler 18 of FIG. 1.

Figure 3:
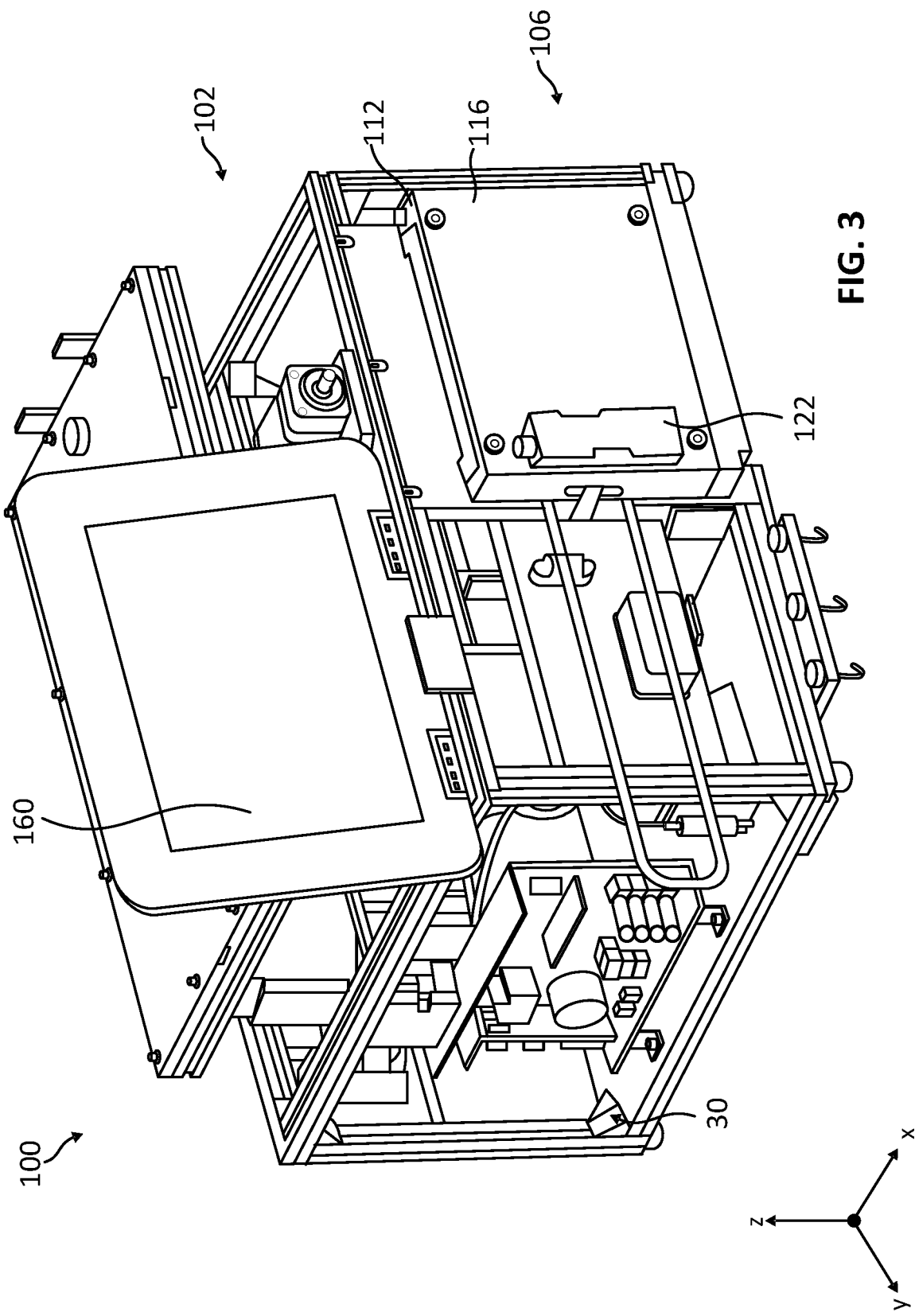
FIG. 3 is a perspective view of an example PD cycler with a PD cassette assembly in an open position.

In the example shown, door assembly 106 is attached to fixed plate assembly 104 via hinge 112 configured to enable door assembly 106 to pivot (e.g., swivel) between a closed position, illustrated in FIG. 3, and an open position, as illustrated in FIG. 2. In some examples, hinge 112 may be attached to one or more supports of PD cycler 100 rather than fixed plate assembly 104, and in some examples door assembly 106 may be configured to move between an open position and a closed position by an action other than pivoting. For example, PD cycler 100 and/or PD cassette assembly 102 may include a mechanism other than hinge 112 configured to allow door assembly 106 to slide, e.g., in any direction within the x-z plane, or to slide towards or away from fixed plate assembly, e.g., in the y-direction. In other examples, PD cassette assembly 102 may include any suitable mechanism to allow door assembly 106 to move towards and away from fixed plate assembly 104 between a closed position and an open position via any suitable method of movement.

Fixed plate assembly 104 is mounted and/or attached to one or more supports of PD cycler 100, and is configured to be stationary with respect to the supports of PD cycler 100. Fixed plate assembly 104 includes a fixed plate, and may include at least one actuator configured to change at least one fluid flow path within cassette 110, and a gasket, as further illustrated in greater detail in FIG. 4. In some examples, the fixed plate includes at least one mount configured to hold the at least one actuator to the fixed plate in a position such that the actuator may occlude a channel of cassette 110 when activated, thereby changing a flow path of cassette 110. The fixed plate is configured to help hold cassette 110 in place relative to fixed plate assembly 104. For example, the fixed plate may include mounting structures configured to position and attach cassette 110 to the fixed plate. The fixed plate may further be configured to hold the gasket, which may be attached to the fixed plate and disposed between the fixed plate and cassette 110. In some examples, the fixed plate and gasket may be substantially planar and may including one or more through holes configured to allow the actuators to extend a pin to occlude a channel of cassette 110 in order to change a flow path of cassette 110.

In some examples, fixed plate assembly 104 further includes latch bar 114. Latch bar 114 is configured to engage with latch 118 to hold door assembly 106 in the closed position. For example, jaws of latch 118 may be configured to receive latch bar 114 and close and hold latch bar 114. In some examples, latch bar 114 may be attached to a support of PD cycler 100 rather than fixed plate assembly 104.

Figure 4:
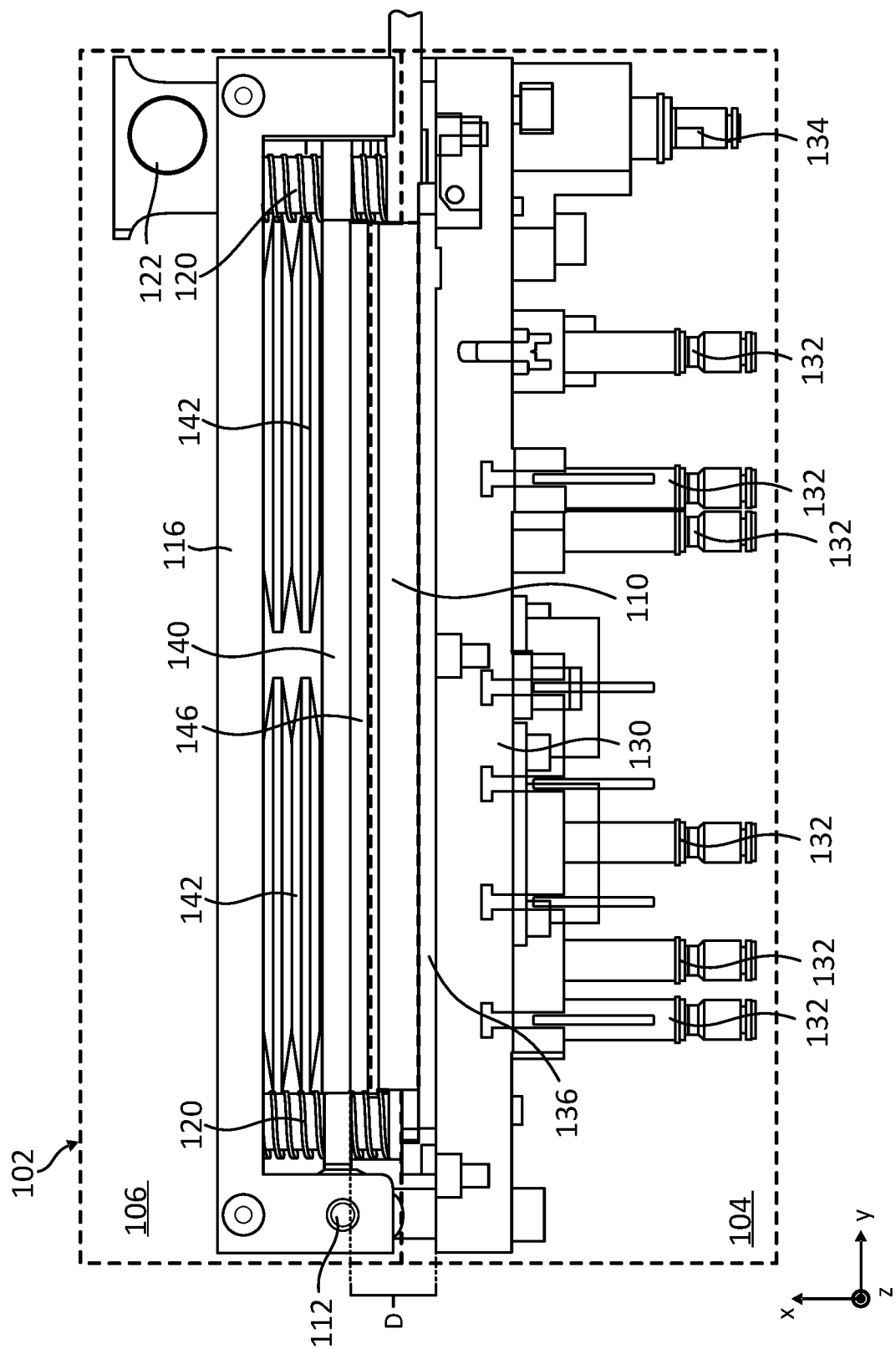
FIG. 4 is a cross-sectional view of an example a PD cassette assembly in a closed position.

In some examples, fixed plate assembly 104 further includes a locking actuator, e.g., as illustrated in greater detail in FIG. 4. The locking actuator is configured to mechanically engage and prevent latch 118 from opening. For example, the locking actuator may extend a pin the mechanically engages and prevents the jaws of latch 118 from opening. In some examples, the locking actuator is a pneumatic actuator configured to extend the pin when air is provided with sufficient air pressure, e.g., from a compressor and under the control of control circuitry 30 (FIG. 1). In some examples, the locking actuator is configured to engage and lock latch 118 when control circuitry 30 causes air to be provided to the bellows of door assembly 106, e.g., to prevent opening of the door assembly 106 while the bellows are inflated such as during a PD therapy session. In some examples, the locking actuator may be attached to a support of PD cycler 100 rather than fixed plate assembly 104.

Door assembly 106 is mounted and/or attached to hinge 112 configured to enable door assembly 106 to move relative to fixed plate assembly 104 between open and closed positions. Door assembly 106 includes frame 116 defining a recess (not visible in the example shown), a movable plate, and at least one bellows configured to inflate and apply a force to the movable plate towards the fixed plate of fixed plate assembly 104 when door assembly 106 is in the closed position. In some examples, door assembly 106 may further include a gasket configured to be attached and held by the movable plate and disposed on the opposite side of the movable plate from the bellows, latch 118, and a counter-force component such as springs 120 configured to apply a force to the movable plate in the opposite direction of the bellows, e.g., to apply a force to the movable plate away from the fixed plate. The movable plate, bellows, gasket, and springs 120 are illustrated in greater detail in FIG. 4.

In some examples, PD cycler 100 includes control circuitry 30, user interface 160, an air compressor and/or pneumatic lines and connections to connect to an external air supply or air compressor. User interface 160 may include display configured to present information to a user and, in some examples, receive input from a user (i.e., may be a touch screen display). In some examples, user interface 160 further includes a keypad, sound receiving circuitry, and/or another mechanism configured to receive input from a user.

PD cassette assembly 102 provides an improvement to the delivery of PD therapy and the sterility of the PD cycler system, and the fluids delivered to a patient, by preventing leaking of fluids. For example, PD cassette assembly 102 is configured to mechanically lock door assembly 106 in the closed position during application of pressure to the cassette, e.g., to prevent the PD cassette mounting assembly from being opened during a fill/drain phase of a PD cycle and while pressure is being applied to the cassette.

FIG. 3 is a perspective view of PD cycler 100 with PD cassette assembly 102 in a closed position. In the example shown, door assembly 106 includes handle 122, which may be attached directly or indirectly to door frame 116. Handle 122 is configured to be manipulable by a user to move door assembly 106 relative to fixed plate assembly 104 between open and closed positions. In some examples, handle 122 is configured to open and close latch 118 (shown in FIG. 2), e.g., a user may operate a mechanism of handle 122 to open and/or close jaws of latch 118. In other examples, latch 118 is configured to open and close, e.g., open and close jaws of latch 118, via contact with latch bar 114, and handle 122 does not include a mechanism to open/close latch 118. For example, latch 118 may be configured to close and grip latch bar 114 when a user moves door assembly 106 to a closed position, and latch 118 may be configured to release latch bar 114 when a user applies a force to move door assembly 106 to an open position.

FIG. 4 is a cross-sectional view of an example a PD cassette assembly 102 in a closed position, where the cross-section is taken along the y-z plane in FIGS. 3 (orthogonal x-y-z axes are shown in the figures for ease of description only). FIG. 4 illustrates door assembly 106 in a closed position relative to fixed plate assembly 104.

Fixed plate assembly 104 includes fixed plate 130, one or more actuators 132, and gasket 136. A plurality of actuators 132 are primarily referred to in the description of FIG. 4. In some examples, fixed plate assembly 104 further includes at least one sensor and a pump mechanism, e.g., configured to provide motive force to fluid within cassette 110. Fixed plate assembly 104 may be mechanically connected to door assembly 106 via hinge 112, as described above. Fixed plate assembly 104 is configured to receive cassette 110 when door assembly 106 is in an open position.

Fixed plate 130 is configured to be opposite movable plate 140 when door assembly 106 is in the closed position. Fixed plate 130 is configured to hold and align cassette 110 relative to actuators 132 and movable plate 140, e.g., when door assembly 106 is in the closed position. For example, fixed plate 130 is configured to align at least one channel of cassette 110 relative to actuators 132 when cassette 110 is mounted to fixed plate 130 such that actuators 132, when activated, engage with cassette 110 to change at least one fluid flow path of the one or more fluid flow paths defined by the channels within cassette 110. In some examples, fixed plate 130 is configured to hold a sensor configured to sense a parameter of a fluid within the cassette, e.g., a fluid temperature and/or a fluid pressure. In some examples, actuators 132 may be pneumatic linear actuators configured to extend, via air pressure, a rod or pin to depress a membrane of cassette 110 into a channel of cassette 110 to occlude the channel when activated. In other examples, actuators 132 may be any other suitable actuator, e.g., spring-loaded pins, solenoids, and the like. Selective occlusion of one or more channels modifies the fluid flow path through cassette 110, and, therefore, through a fluid circuit of PD cycler 100. That is, selective occlusion of one or more channels of cassette 110 by one or more actuators 132 closes certain fluid flow paths to prevent fluid from flowing through those flow paths and enable fluid to flow through other, open flow paths. Thus, by occluding different channels of cassette 110, actuators 132, under the control of control circuitry 30 (FIG. 1) or other control circuitry, can define different flow paths through cassette 110.

Gasket 136 is attached and/or mounted to fixed plate 130, disposed between fixed plate 130 and movable plate 140, and configured to contact cassette 110. Gasket 136 may be made of a compressible, flexible material and may be configured to planarize the contact between gasket 136 and cassette 110, e.g., in order to provide a substantially even pressure across the surface area of cassette 110 and seal a membrane of cassette 110 to a rigid substrate of cassette 110. Gasket 136 may be further configured to protect cassette 110 from damage during application of pressure to cassette 110. Gasket 146 is attached and/or mounted to movable plate 140, disposed between movable plate 140 and fixed plate 130, and configured to contact cassette 110. Gasket 146 may be made of the same and/or a different compressible, flexible material as gasket 136 and may be configured to planarize the contact between gasket 146 and cassette 110, e.g., in order to provide a substantially even pressure across the surface area of cassette 110. Gasket 146 may be further configured to protect cassette 110 from damage during application of pressure to cassette 110.

In some examples, cassette 110 includes a substantially rigid substrate (e.g., a "body") defining a plurality of fluid channels, e.g., a metal, a molded plastic, or any suitable material with sufficient rigidity and capable of defining the channels. Cassette 110 may further include a flexible membrane covering the plurality of channels. The flexible membrane may cover substantially all of the surface area of the face of the rigid substrate defining the plurality of fluid channels and may be configured, when a pressure is applied to the membrane towards the rigid substrate, to seal to the structure of the substrate and prevent fluid from leaking and/or flowing out of the channels of the substrate. The membrane may be further configured to be depressible, that is, when a pressure is applied to substantially all of the area of the membrane, a localized pressure, such as by a pin or rod extended from an actuator, may flex a local portion of the membrane into the channel to occlude the channel. The end of the rod or pin of the actuator may have a shape that conforms to the shape of the channel such that when activated, the rod or pin may depress the membrane into the channel to block the channel and prevent fluid from flowing and/or leaking into the channel.

Gaskets 136 and 146 may be configured to provide a substantially even pressure across the surface area of the first and second major surfaces, e.g., the front and back surfaces, of cassette 110. For example, PD cassette assembly 102 may apply pressure to seal the membrane of cassette 110 to the rigid substrate of cassette 110 by moving and/or applying a force to movable plate 140 towards fixed plate 130. To apply sufficient pressure to the membrane of cassette 110 over the entire surface area of the membrane in order to seal the entire surface area of the membrane to the rigid substrate, and without adversely impacting the structural integrity of at least localized portions of cassette 110, movable plate 140 and fixed plate 130 may be configured to be substantially planar or configured to conform the surface shape of cassette 110. Further, movable plate 140 and fixed plate 130 may be configured to be aligned, that is with opposing surfaces substantially parallel when door assembly 106 is in the closed position.

In some examples, movable plate 140 and fixed plate 130 may be rigid plates. Tolerances for rigid plates, e.g., metal plates, for both surface roughness and alignment relative to one another to provide a substantially even pressure to cassette 110 between the plates may be relatively high. Gaskets 136 and 146 may allow the tolerances of movable plate 140 and fixed plate 130 for surface roughness and alignment to be relaxed. Gaskets 136 and 146 may be configured to substantially distribute nonuniformities in applied pressure between movable plate 140 and fixed plate 130 across an area, e.g., to even out pressure nonuniformities across the front and back surface area of cassette 110 due to surface roughness and/or misalignment of movable plate 140 and fixed plate 130. Gaskets 136 and 146 may have the same and or different durometers, and the durometers of gaskets 136 and 146 may be configured to substantially transfer the force applied by movable plate 140 and fixed plate 130 to cassette 110 while reducing the nonuniformity of the force applied to cassette 110.

In the example shown, fixed plate assembly 104 further includes a locking actuator 134. Locking actuator 134 is configured to mechanically engage and prevent latch 118 (FIGS. 1, 6-11) from opening, as further illustrated in FIGS. 6-11. For example, the locking actuator may extend a pin the mechanically engages and prevents the jaws of latch 118 from opening. In some examples, the locking actuator may be a pneumatic actuator configured to extend the pin when air is provided with sufficient air pressure. In some examples, the locking actuator is configured to engage and lock latch 118 when air is provided to the bellows of door assembly 106, e.g., to prevent opening of the door assembly while the bellows are inflated such as during a PD therapy session. In other examples, locking actuators 134 may be any other suitable actuator, e.g., a spring-loaded pin, a solenoid, and the like. In some examples, the locking actuator may be attached to a support of PD cycler 100 rather than fixed plate assembly 104.

In some examples, fixed plate 130 and gasket 136 may include through holes configured to allow a pin, rod, or other structure of actuators 132 to extend through fixed plate 130 and gasket 136 to occlude a flow path of cassette 110. Fixed plate 130 and gasket 136 may further include through holes configured to allow sensors to sense a parameter of a fluid within cassette 110.

Door assembly 106 includes frame 116, bellows 142, movable plate 140 (also referred to herein as an opposing plate), gasket 146, counter-force components 120, and handle 122. In the example shown, door assembly 106 is connected to fixed plate assembly 104 via hinge 112. Hinge 112 is configured to enable door assembly 106 to move towards and away from fixed plate assembly 104 between open and closed positions. In the example shown, hinge 112 is configured to allow door assembly 106 to swivel and/or swing towards and away from fixed plate assembly 104, e.g., in the x-y plane and about an axis parallel with the z-axis.

Frame 116 is a structure that, in the example of FIG. 4, defines a recess configured to house bellows 142, movable plate 140, gasket 146, and counter-force components 120. That is, bellows 142, movable plate 140, gasket 146, and counter-force components 120 may be disposed within the recess defined by frame 116. Frame 116 may be a rigid structure, such as a metal, a composite, a rigid plastic, or any suitably rigid material capable of housing bellows 142, movable plate 140, gasket 146, and counter-force components 120 and provide a backing for bellows 142 to push against in order to provide a force to movable plate 140 in the direction of fixed plate 130 when door assembly 106 is in the closed position.

In the example shown, door assembly 106 is in the closed position, and latch 118 (not shown in FIG. 4) is latched to a latch bar of fixed plate assembly 104. In the closed position, with bellows 142 deflated, door assembly 106 is configured to hold movable plate 140 separated from fixed plate 130 by a distance D, which may be a predetermined distance. In some examples, distance D may include an air gap between gasket 146 and cassette 110 mounted on fixed plate assembly 104. In other examples, distance D may not include an air gap and gasket 146 may contact cassette 110 when door assembly 106 is in the closed position.

Movable plate 140 is disposed within the recess define by frame 116. Movable plate 140 is configured to move towards and away from fixed plate 130 when door assembly 106 is in the closed position. For example, movable plate 140 may be mounted on guide pins and may be configured to move along the guide pins. Other structures can be used to provide such motion of movable plate 140 towards fixed plate 130 in other examples.

One or more bellows 142 are disposed between movable plate 140 and an surface of frame 116. Bellows 142 are configured to inflate to apply a force to movable plate 140 towards fixed plate 130 when door assembly 106 is in the closed position. For example, an air compressor of PD cycler 100 may be pneumatically connected to bellows 142, may provide air to bellows 142 to expand bellows 142, e.g., under the control of control circuitry 30. When inflated, bellows 142 may push against the inner surface of frame 116 which may be configured to be non-movable, thereby forcing bellows 142 to expand in the direction towards movable plate 140. Bellows 142 may expand and provide a force to movable plate 140 that is greater than the force provided by counter-force components 120, thereby applying an increased pressure (e.g., from atmospheric pressure) across the major surfaces of cassette 110 through gaskets 146, 136 and sealing the membrane of cassette 110 to one or more structures of the rigid substrate of cassette 110, thereby defining one or more fluid flow paths of cassette 110, e.g., the fluid flow paths conforming to channels within cassette 110. In some examples, bellows 142 are configured to provide a pressure of up to 100 pounds of force, greater than or equal to 100 pounds of force, greater than or equal to 200 pounds of force, greater than or equal to 250 pounds of force, greater than or equal to 300 pounds of force, or any suitable pressure to seal the membrane to one or more structures of the rigid substrate of cassette 110 and define one or more fluid flow paths of cassette 110. For example, bellows 142 may be configured to provide a pressure less than or equal to about 256 pounds of force (about 1138.74 Newtons) on a side or major surface of cassette 110. The example shown in FIG. 4 illustrates two bellows 142, however, in some examples door assembly 106 may include fewer or more bellows 142, e.g., one bellows 142 or three or more bellows 142. In some examples, bellows 142 are configured to apply a force to movable plate 140 such that movable plate 140 and fixed plate 130 apply a 200 kilogram (kg) force on cassette 110. In other examples, bellows 142 may be configured to apply a lesser or greater force to movable plate 140, resulting in a s lesser or greater force applied to cassette 110.

Counter-force components 120 are be configured to provide a force to movable plate 140 away from fixed plate 130. For example, with bellows 142 deflated and door assembly 106 in the closed position, counter-force components 120 are configured to hold movable plate 140 at the distance D, which can be a predetermined and fixed distance D, from fixed plate 130. In the example shown, counter-force components 120 comprise a plurality of springs disposed on the guide pins. A first set of springs are configured to push movable plate 140 away from the inner surface of the recess defined by frame 116, and another set of springs are configured to push movable plate 140 towards that inner surface. The force from each set of springs may be balanced, or equal, when movable plate 140 is a distance D from fixed plate 130 when door assembly 106 is in the closed position and bellows 142 are deflated. When bellows 142 are inflated, bellows 142 push movable plate 140 towards fixed plate 130. When bellows 142 are deflated from being inflated, counter-force components 120 are configured to provide a force in the opposite direction of bellows 142 in order to reduce the pressure applied to cassette 110 and/or move movable plate 140 to the distance D from fixed plate 130. In other examples, counter-force components 120 may be any suitable force-providing components, e.g., pneumatic actuators, solenoids, and the like.

Handle 122 is attached to frame 116, and is configured to allow a user to move door assembly 106 between open and closed positions. In some examples, door assembly 106 may include a latch, e.g., latch 118, and handle 122 may include a mechanism which a user may manipulate to open and close the latch, such as a knob. In some examples, latch 118 is configured to lock upon and during inflation of bellows 142, and handle 122 may be configured to prevent a user from moving door assembly 106 to an open position while bellows 142 are inflated, e.g., handle 122 cannot bypass the locking mechanism of the latch. For example, locking actuator 134 may be configured to extend a locking pin to prevent jaws of the latch from opening while air is provided to bellows 142 to inflate bellows 142.

Figure 5:
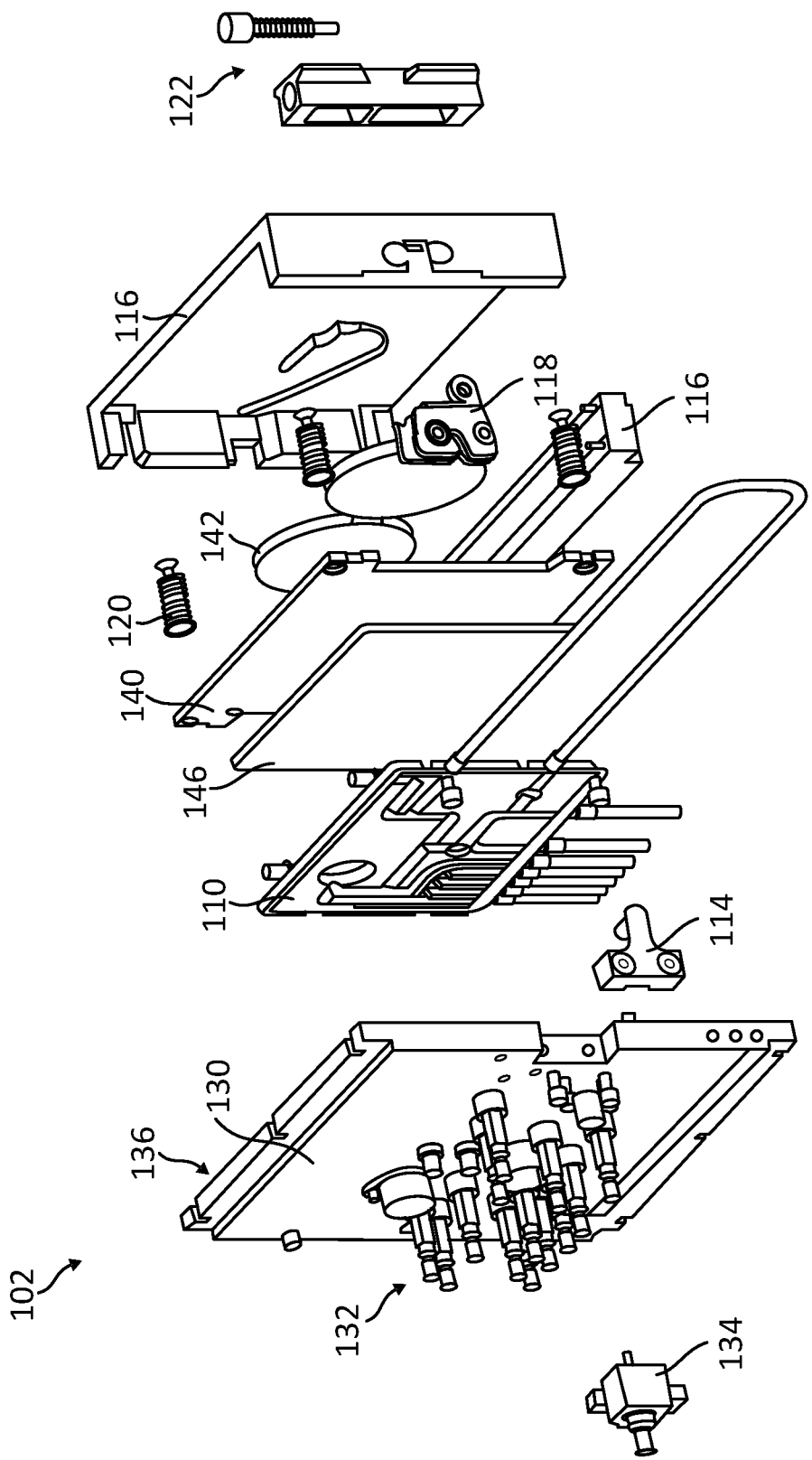
FIG. 5 is an exploded perspective view of an example a PD cassette assembly.

FIG. 5 is an exploded perspective view of an example a PD cassette assembly 102. The example shown in FIG. 5 illustrates individual components of PD cassette assembly 102. PD cassette assembly 102 includes locking actuator 134 and latch bar 114 which may be configured to be mounted to and/or attached to fixed plate 130. Actuators 132 and one or more sensors may be configured to be mounted to fixed plate 130. Fixed plate 130 is configured to be disposed opposite movable plate 140 (when door assembly 106 is in the closed position), and gasket 136 is configured to be attached to fixed plate 130 between fixed plate 130 and movable plate 140. Fixed plate 130 is configured to help receive and help mount cassette 110 between fixed plate 130 and movable plate 140.

Gasket 146 is configured to be attached to movable plate 140 between fixed plate 130 and movable plate 140. Movable plate 140 is configured to be disposed within a recess defined by frame 116, and one or more counter-force components 120 are configured to hold movable plate 140 a distance D from fixed plate 130 when door assembly 106 is in a closed position and bellows 142 are deflated. Latch 118 is configured to latch to latch bar 114 and hold door assembly 106 in the closed position, and bellows 142 are configured to inflate and apply a force to movable plate 140 in the direction of fixed plate 130. Handle 122 is configured to be mounted to frame 116 and allow a user to move door assembly 106 relative to fixed plate 130, and handle 122 may be further configured to allow a user to manipulate latch 118 to open and close and thereby latch and release door assembly 106 from latch bar 114.

Figure 7:
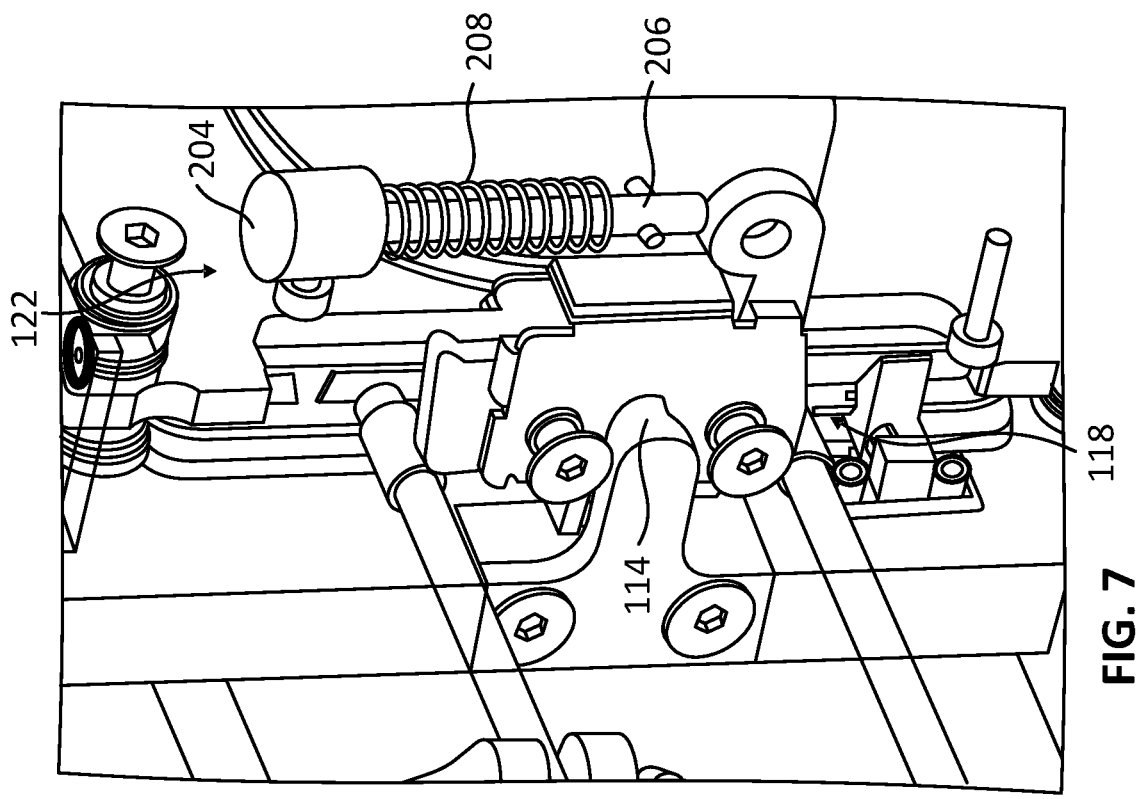
FIG. 7 is a perspective view of the example handle of FIG. 6 with the handle cover removed to show further detail of the handle.
Figure 6:
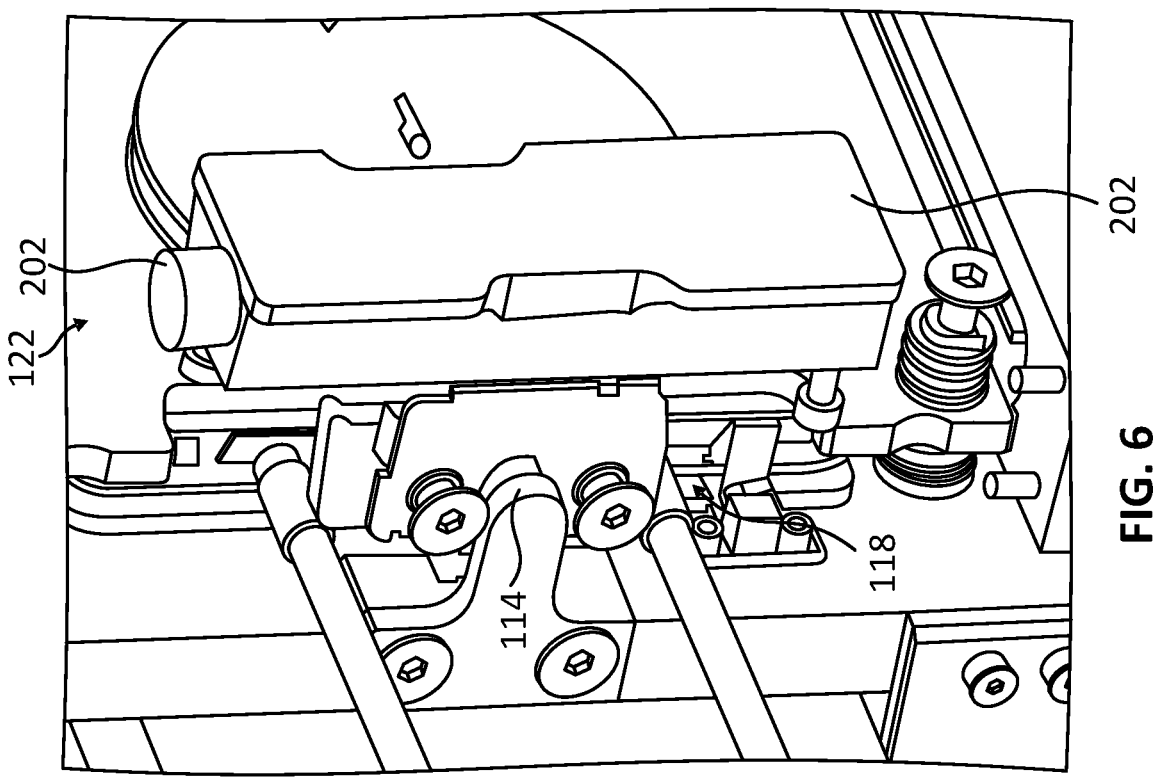
FIG. 6 is a perspective view of an example handle of a PD cassette assembly.
Figure 8:
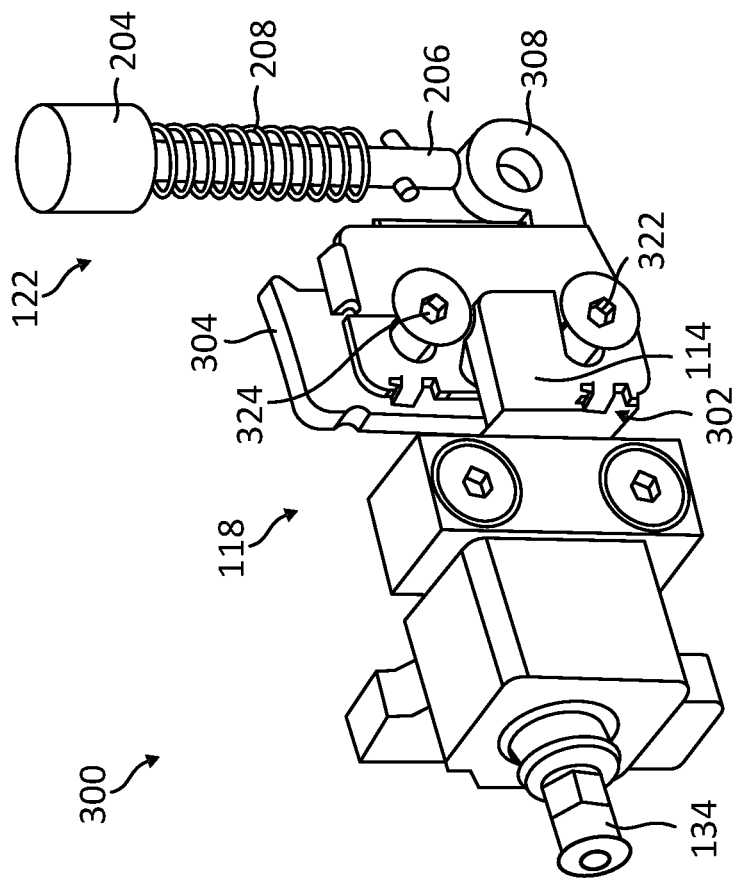
FIG. 8 is a perspective view of an example latch and lock assembly of a PD cassette assembly.
Figure 9:
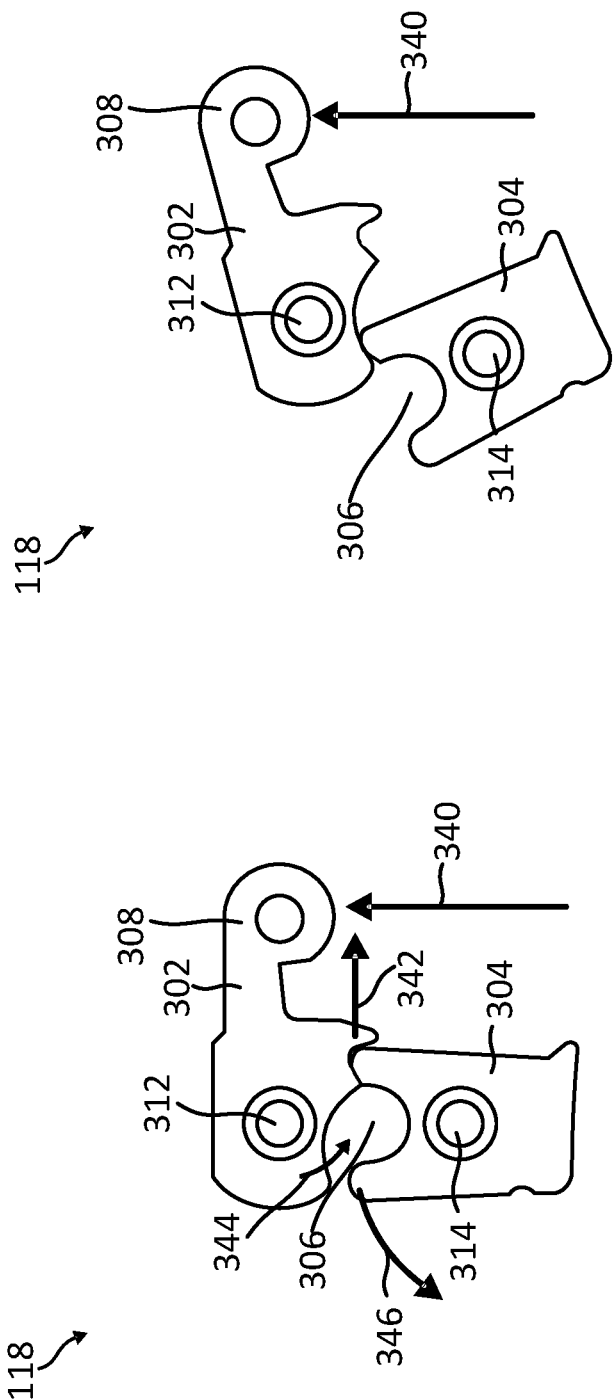
FIG. 9A is a cross-sectional side view illustrating a portion of an example latch in a closed position.
FIG. 9B is a cross-sectional side view illustrating a portion of an example latch in an open position.
Figure 10:
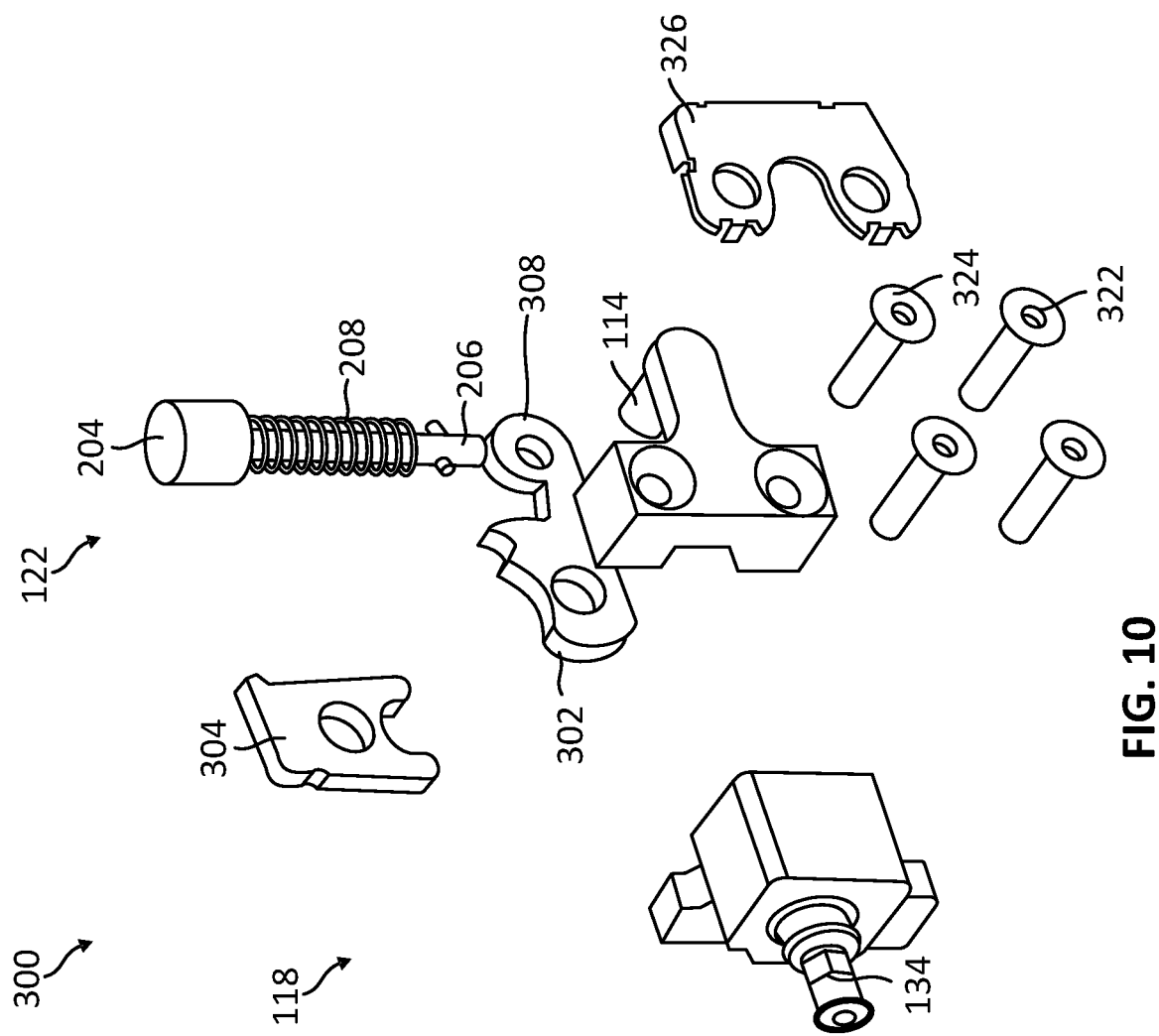
FIG. 10 is an exploded perspective view of the example a latch and lock assembly of PD cassette assembly.
Figure 11:
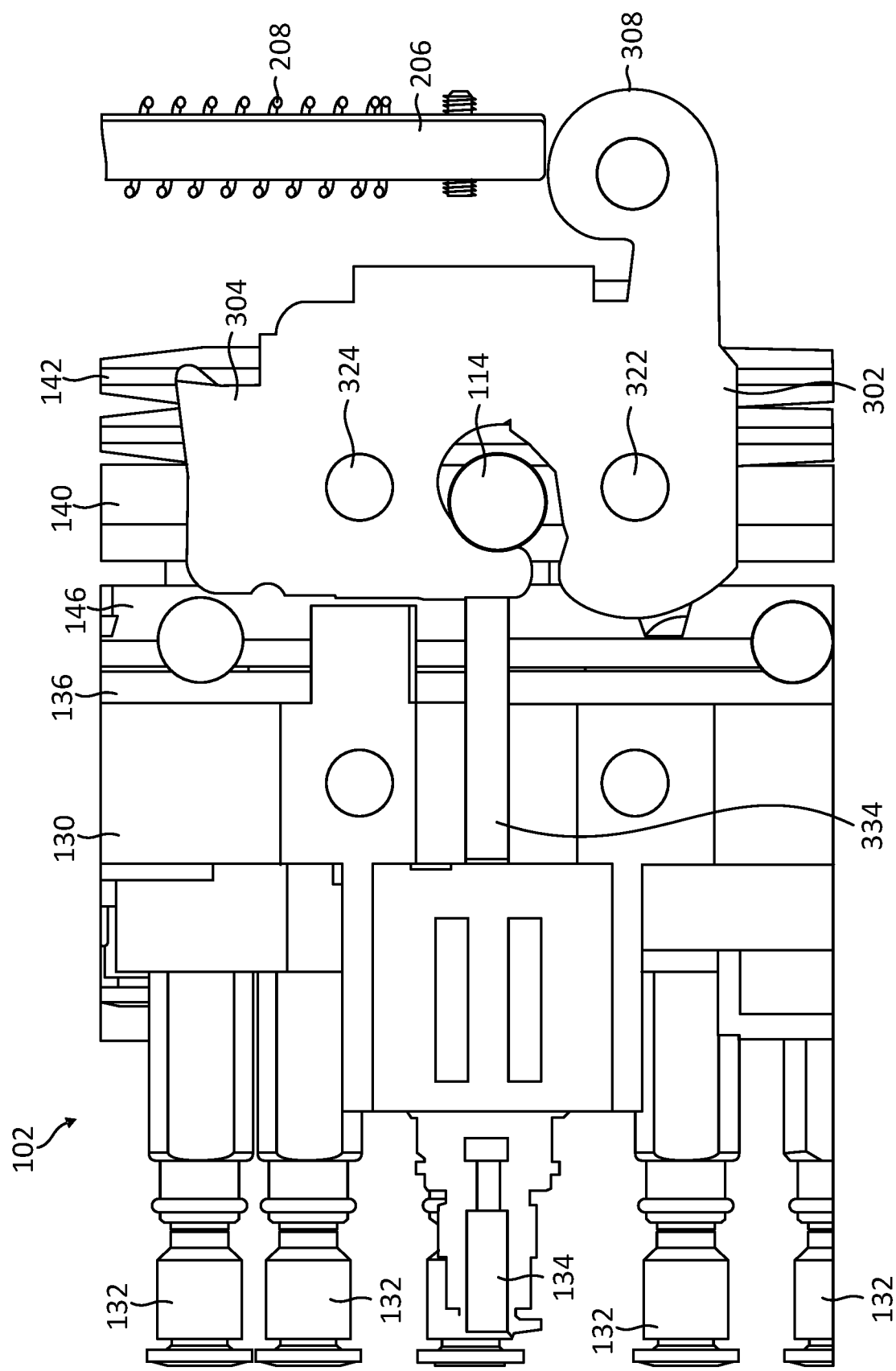
FIG. 11 is a cross-sectional view of the example latch and lock assembly of FIG. 8 in a closed and locked position.

FIGS. 6-11 illustrate various perspective and cross-sectional views of an example latch and lock assembly 300, e.g., latch 118, latch bar 114, handle 122, and locking actuator 134. FIGS. 6-11 are described concurrently below. FIG. 6 is a perspective view of an example handle 122 of a PD cassette assembly 102. FIG. 7 is a perspective view of the example handle 122 of FIG. 6 with the handle cover 202 removed to show further detail of handle 122. FIG. 8 is a perspective view of an example latch and lock assembly 300 of PD cassette assembly 102. FIG. 9A is a cross-sectional side view illustrating a portion of an example latch 118 in a closed position. FIG. 9B is a cross-sectional side view illustrating a portion of an example latch in an open position. FIG. 10 is an exploded perspective view of the example a latch and lock assembly 300 of PD cassette assembly 102. FIG. 11 is a cross-sectional view of the example latch and lock assembly 300 of FIG. 8 in a closed and locked position.

Handle 122 includes cover 202, knob 204, rod 206, and spring 208. Handle 122 may be configured to mount and/or attach to frame 116. Cover 202 is configured to house knob 204, rod 206, spring 208, and at least partially house one or more components of latch 118. Cover 202 may further be configured to be gripped and/or held by a user, e.g., to open and close door assembly 106. Knob 204 is connected to rod 206 and is configured to extend at least partially out of cover 202. Knob 204 is configured to be depressed by a user, thereby pushing push rod 206 to contact and move jaws of latch 118. Spring 208 is configured to retain knob 204 and rod 206 in a closed position, that is, such that the jaws of latch 118 are closed. For example, when knob 204 is not depressed, spring 208 biases knob 204 and rod 206 away from the jaws of latch 118 allowing the jaws to close, and when a user depressed knob 204, rod 206 forces the jaws of latch 118 to open. Although handle 122 illustrates knob 204 and rod 206 as a linear mechanism, other mechanism may be used to open and close the jaws of latch 118 as well. For example, knob 204 may be a knob that may be turned or twisted to move rod 206.

FIG. 8 illustrates an example latch and lock assembly 300. Latch and lock assembly 300 includes locking actuator 134, latch bar 114, latch 118, and handle 122. In some examples, latch and lock assembly 300 may be distributed between fixed plate assembly 104 and door assembly 106. For example, locking actuator 134 and latch bar 114 may be mounted and/or attached to fixed plate assembly 104, and latch 118 and handle 122 may be mounted and/or attached to door assembly 106 and may move with door assembly 106 when door assembly 106 is moved between open and closed positions.

In the example shown, latch 118 includes first jaw 302 and second jaw 304 (collectively referred to as jaws 302, 304) configured to counter rotate relative to each other, e.g., in response to manipulation of handle 122, to open and close an aperture 306. Aperture 306 (illustrated in FIG. 9A) is configured to receive and release latch bar 114 in an open position, and latch onto, or capture or hold, latch bar 114 in a closed position. First jaw 302 is configured to rotate about pin 322, and second jaw 304 is configured to rotate about pin 324. First jaw 302 may also include a lever arm 308. Rod 206 may be configured to contact and push lever arm 308, e.g., to open jaws 302, 304.

Locking actuator 134 and latch bar 114 may be configured to align with latch 118 when door assembly 106 is in the closed position. For example, locking actuator 134 and latch bar 114 are mounted and position on fixed plate assembly 104 such that latch bar 114 is received within aperture 306 when door assembly 106 is moved to the closed position, and locking actuator 134 is mounted and positioned such that lock pin 334 (illustrated in FIG. 11) may contact jaws 302, 304 when door assembly 106 is in the closed position and when jaws 302, 304 are in the closed position.

FIG. 9A further illustrates how a force applied to the jaws of latch 118, e.g., via rod 206, may open the jaws. FIG. 9B is a cross-sectional side view illustrating a portion of an example latch in an open position. As shown in FIG. 8, a first jaw 302 includes a lever arm 308 and through hole 312. First jaw 302 is configured to rotate about pin 322 (FIG. 9A) disposed in through hole 312, e.g., with application of a force to lever arm 308. Second jaw 304 includes through hole 314 and is configured to rotate about pin 324 (FIG. 9A) disposed in through hole 314. First and second jaws 302, 304 are disposed relative to each other, and are each configured so as to form aperture 306 when first and second jaws 302, 304 are in a closed position, as shown. First and second jaws 302, 304 are configured to receive latch bar 114 within aperture 306, e.g., in an open position, and to latch and/or hold onto latch bar 114 when in a closed position.

To open first and second jaws 302, 304 (e.g., to move between the closed position shown in FIG. 9A and the open position shown in FIG. 9B), rod 206 is configured to apply a force to lever arm 308 (e.g., in response to user depression of rod 206), e.g., as illustrated by arrow 340. The force causes first jaw 302 to rotate about pin 322 within through hole 312, causing at least a portion of jaw 302 to move in the direction denoted by arrow 344. Concurrently, a concave portion of first jaw 302 is caused to move in a direction denoted by arrow 342, e.g., out of the way of second jaw 304 and allowing second jaw 304 to rotate about pin 324 within through hole 314 in the direction indicated by arrow 346. At least a portion of jaw 304 then rotates in the direction indicated by arrow 346, causing aperture 306 to allow latch bar 114 to be received and released. In other words, in a closed position, the separation between jaws 302, 304 is less than the minimum dimension, e.g., the radius, of latch bar 114 and prevents latch bar 114 from being released from aperture 306. In an open position, e.g., when knob 204 is depressed to open jaws 302, 304, the separation between jaws 302, 304 is greater than the maximum dimension of latch bar 114 and allowing latch bar 114 to be released from, or received into, aperture 306. In some examples, only one jaw 302 or 304 may move in order to open and close access to aperture 306.

FIG. 10 is an exploded perspective view of the example a latch and lock assembly 300 of PD cassette assembly 102, and illustrates individual components of latch and lock assembly 300. Latch and lock assembly 300 includes locking actuator 134 and latch bar 114 which may be configured to be mounted to and/or attached to fixed plate 130. Latch 118 includes first jaw 302 and second jaw 304. First jaw 302 may be mounted to frame 116 of door assembly 106 via pin 322 and may be configured to rotate about pin 322, and may include lever arm 308. Second jaw 304 may be mounted to frame 116 of door assembly 106 via pin 324 and may be configured to rotate about pin 324. Handle 122 includes knob 204, spring 208, and rod 206. Rod 206 is configured to push down on lever arm 308 to open jaws 302, 304 when knob 204 is pressed, e.g., knob 204 may be a push button. Spring 208 is configured to push rod 206 away from lever arm 308 when knob 204 is released, thereby allowing jaws 302, 304 to close.

FIG. 11 is a cross-sectional view of the example latch and lock assembly 300 of FIG. 8 mounted to PD cassette assembly 102 with door assembly 106 in the closed position, latch 118 in the closed position, and locking actuator 134 activated to lock latch 118. In the example shown, locking actuator 134 is activated to extend lock pin 334. Lock pin 334 blocks jaws 302, 304 from opening. For example, if a user pressed knob 204 to push rod 206 and lever arm 308, lock pin 334 in the activated, locked, or extended position may mechanically block and/or prevent jaws 302, 304 from opening.

In some examples, locking actuator 134 is activated when bellows 142 are inflated, e.g., control circuitry 30 causes a compressor (or any other suitable pressurized air source) to provide pressurized air to locking actuator 134 to extend lock pin 334 when air is provided to bellows 142. Similarly, when air is no longer provided to bellows 142, e.g., control circuitry 30 causes the pressurized air to no longer by applied to bellows 142, air may no longer be provided to locking actuator 134 and lock pin 334 may retract. In some examples, control circuitry 30 simply causes the compressor to stop applying the pressurized air to bellows 142 and bellows 142 may naturally deflate, while in other examples, control circuitry 30 may cause active depressurization of bellows 142. In some examples, locking actuator 134 may be configured to stay activated to extend lock pin 334 and lock latch 118 and door assembly 106 in the closed positions while air is no longer provided to bellows 142 and until bellows 142 depressurize, e.g., until bellows 142 are deflated/depressurized to a pressure that is equal to or below threshold pressure.

In some examples, lock pin 334 may contact first jaw 302, second jaw 304, or both, to block jaws 302, 304 from opening. In other examples, lock pin 334 may extend far enough such that the distal end of lock pin 334 (e.g., the end farthest from locking actuator 134) does not contact jaws 302, 304, but is close enough such that jaws 302, 304 contact and are blocked by lock pin 334 from opening enough to release latch bar 114.

Figure 12:
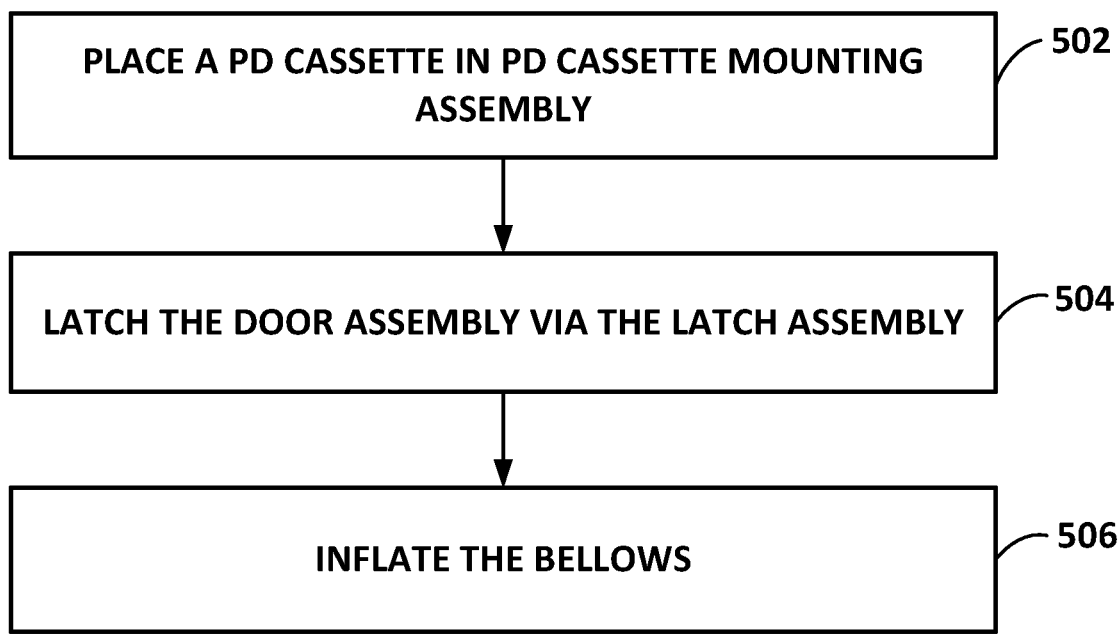
FIG. 12 is a flow diagram of an example method using an example PD cassette mounting assembly and latch and lock.

FIG. 12 is a flow diagram of an example method using an example PD cassette mounting assembly and latch and lock. The example technique of FIG. 12 is described with respect to PD cycler 100 of FIGS. 2 and 3, PD cassette assembly 102 of FIG. 4, and latch and lock assembly 300 of FIG. 8, the example technique of FIG. 12 may be performed with any type of PD cycler 100 that includes a cassette mounting assembly and lock and latch assembly described herein. In some examples, the technique of FIG. 12 may be performed by user operating a PD cycler.

A user may place a PD cassette in a PD mounting assembly (502). For example, the PD mounting assembly may be PD cassette assembly 102 of PD cycler 100 as described above, and a user may place and/or mount cassette 110 to fixed plate 130. PD cassette assembly 102 may be configured to position cassette 110 between fixed plate 130 and movable plate 140 when placed and/or mounted to fixed plate 130.

The user may latch a door assembly via a latch assembly (504). For example, the PD cassette assembly 102 may include fixed plate assembly 104 and door assembly 106 as described above, and the user may pivot door assembly 106 from an open position to a closed position, and may operate latch 118 to latch door assembly 106 in the closed position. For example, the user may swivel door assembly 106 shut, e.g., to the closed position and depress knob 204 to open jaws 302, 304 to receive latch bar 114 within aperture 306. When door assembly is in the closed position with latch bar 114 received within aperture 306, the user may release knob 204 allowing jaws 302, 304 to close and thereby retain latch bar 114 within aperture 306, thereby retaining door assembly 106 in the closed position.

The user may operate a PD cycler to inflate bellows (506). For example, the user may interact with a user interface 160 of PD cycler 100 to begin PD therapy. In response to the user interaction, control circuitry 30 of PD cycler 100 causes an air compressor and/or pump to provide pressurized air to bellows 142, causing bellows 142 to inflate. Bellows 142, by virtue of inflating, applies a force to movable plate 140 towards fixed plate 130, causing both movable plate 140 and fixed plate 130 to apply a pressure to seal a cassette membrane of cassette 110 to cassette 110 and define one or more fluid flow patch within cassette 110.

In some examples, control circuitry 30 of PD cycler 100 causes the air compressor and/or pump to provide pressurized air to locking actuator 134 concurrently with providing air to bellows 142, activating locking actuator 134 and causing lock pin 334 to extend and lock latch 118 in the closed position, e.g., to prevent jaws 302, 304 from opening to release latch bar 114, thereby locking door assembly 106 in the closed position. Locking actuator 134 may stay activated while air is provided to bellows 142, and may unlock when air is no longer provided to bellows 142. In some examples, locking actuator 134 may stay activated and extend lock pin 334 to lock latch 118 and door assembly 106 in the closed positions while air is no longer provided to bellows 142 and until bellows 142 depressurize, e.g., until bellows 142 are deflated/depressurized to a pressure that is equal to or below threshold pressure.

The techniques described in this disclosure, including those attributed to PD cycler 18, control circuitry 30, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry"

may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. An assembly comprising:
    a first assembly comprising:
        a frame defining a recess;
        a first plate disposed within the recess; and
        a bellows disposed between the first plate and an inner surface of the frame;
    a second assembly comprising a second plate configured to be opposite the first plate when the first assembly is in a closed position relative to the second assembly, wherein the first assembly is configured to move relative to the second assembly between an open position and the closed position;
    a latch bar attached to the second assembly; and
    a latch assembly configured to hold the first assembly to the second assembly in the closed position, the latch assembly comprising:
        first and second jaws configured to receive the latch bar when the first and second jaws are open, wherein the first and second jaws are configured to close and hold the latch bar when the first and second jaws are latched closed, wherein the latch assembly is configured to hold the first assembly to the second assembly in the closed position when the first and second jaws are latched closed and holding the latch bar, and wherein the latch assembly is configured to lock the first assembly in the closed position when the bellows applies a force to the first plate; and
        an actuator configured to extend a pin configured to mechanically engage and prevent the first and second jaws from opening while the bellows applies a force to the first plate, wherein the actuator is configured to retract the pin to enable the first and second jaws to open while the bellows is not applying the force to the first plate,
    wherein the bellows is configured to inflate to apply a force to the first plate towards the second plate when the first assembly is in the closed position.

2. The assembly of claim 1, wherein the assembly is configured to receive a cassette when the first assembly is in the open position.

3. The assembly of claim 2, further comprising the cassette.

4. The assembly of claim 1, wherein the first assembly further comprises a first gasket disposed on the first plate between the first plate and the second plate, and wherein the second assembly further comprises a second gasket disposed on the second plate between the second plate and the first plate.

5. The assembly of claim 4, wherein the assembly is configured to receive a cassette when the first assembly is in the open position, and wherein the assembly is configured to hold the cassette between the first gasket and the second gasket when the first assembly is in the closed position.

6. The assembly of claim 1, wherein the actuator is a pneumatic actuator pneumatically connected to a compressor, wherein the bellows is pneumatically connected to the compressor, and wherein the actuator is configured to extend the pin when the compressor provides air to the bellows.

7. The assembly of claim 1, wherein the assembly is configured to hold a cassette between the first plate and the second plate when the first assembly is in the closed position, the cassette comprising a cassette membrane and a cassette housing, and wherein when the cassette is positioned between the first plate and the second plate and the first assembly is in the closed position, the force is sufficient to cause the first plate to apply a pressure to seal the cassette membrane to the cassette housing and selectively block one or more fluid flow paths within the cassette.

8. The assembly of claim 7, wherein the second plate is configured to hold a linear actuator in a position such that the linear actuator, when activated, changes at least one fluid flow path of the one or more fluid flow paths within the cassette, wherein the second plate is configured to hold a sensor configured to sense a parameter of a fluid within the cassette.

9. A peritoneal dialysis cassette mounting assembly comprising:
    a first plate;
    a second plate opposing the first plate and separate from the first plate by a predetermined distance, wherein the first plate is configured to move towards or away from the second plate;
    a bellows disposed opposite the first plate from the second plate and configured to apply a force to the first plate towards the second plate upon inflation;
    a latch bar; and
    a latch assembly comprising:
        first and second jaws configured to receive the latch bar when the first and second jaws are open, wherein the first and second jaws are configured to close and hold the latch bar when the first and second jaws are latched closed, wherein the latch assembly is configured to hold the first plate and the second plate in a closed position when the first and second jaws are latched closed and holding the latch bar; and
        an actuator configured to extend a pin configured to mechanically engage and prevent the first and second jaws from opening while the bellows applies the force to the first plate, wherein the actuator is configured to retract the pin to enable the first and second jaws to open while the bellows is not applying the force to the first plate.

10. The peritoneal dialysis cassette mounting assembly of claim 9 further comprising:

a first assembly comprising a frame configured to hold the first plate; and
a second assembly comprising a frame configured to hold the second plate,
wherein the first assembly is configured to move relative to the second assembly between an open position and the closed position.

11. The peritoneal dialysis cassette mounting assembly of claim 10, wherein the latch assembly is configured to hold the first assembly to the second assembly in the closed position and to lock the first assembly in the closed position when the bellows applies the force to the first plate.

12. The peritoneal dialysis cassette mounting assembly of claim 10, wherein the peritoneal dialysis cassette mounting assembly is configured to hold a cassette between the first plate and the second plate when the first assembly is in the closed position, the cassette comprising a cassette membrane and a cassette housing, and wherein when the cassette is positioned between the first plate and the second plate and the first assembly is in the closed position, the force is sufficient to cause the first plate to apply a pressure to seal the cassette membrane to the cassette housing and define one or more fluid flow paths within the cassette.

13. The peritoneal dialysis cassette mounting assembly of claim 12, wherein the second plate is configured to hold a linear actuator in a position such that the linear actuator, when activated, changes at least one fluid flow path of the one or more fluid flow paths within the cassette, wherein the second plate is configured to hold a sensor configured to sense a parameter of a fluid within the cassette.

14. The peritoneal dialysis cassette mounting assembly of claim 12, further comprising the cassette.

15. The peritoneal dialysis cassette mounting assembly of claim 9, wherein the actuator includes a pneumatic actuator pneumatically connected to a compressor, wherein the bellows is pneumatically connected to the compressor, and wherein the actuator is configured to extend the pin when the compressor provides air to the bellows.

16. A method comprising:
placing a peritoneal dialysis cassette in a peritoneal dialysis cassette mounting assembly, the peritoneal dialysis cassette mounting assembly comprising:
a door assembly comprising:
a frame defining a recess;
first plate disposed within the recess; and
a bellows disposed between the first plate and an inner surface of the frame;
a fixed plate assembly comprising a second plate configured to be opposite the first plate when the door assembly is in a closed position relative to the fixed plate assembly,
wherein the door assembly is configured to move relative to the fixed plate assembly between an open position and the closed position;
a latch bar attached to the fixed plate assembly; and
a latch assembly configured to hold the door assembly the fixed plate assembly in the closed position, the latch assembly comprising:
first and second jaws configured to receive the latch bar when the first and second jaws are open, wherein the first and second jaws are configured to close and hold the latch bar when the first and second jaws are latched closed, wherein the latch assembly is configured to hold the door assembly to the fixed plate assembly in the closed position when the first and second jaws are latched closed and holding the latch bar; and
an actuator configured to extend a pin configured to mechanically engage and prevent the first and second jaws from opening while the bellows applies a force to the first plate, wherein the actuator is configured to retract the pin to enable the first and second jaws to open while the bellows is not applying the force to the first plate,
wherein the peritoneal dialysis cassette is placed between the first plate and the second plate when the door assembly is in the closed position,
wherein the bellows is configured to inflate to apply the force to the first plate towards the second plate when the door assembly is in the closed position;
latching, via the latch assembly, the door assembly; and
causing the bellows to inflate to cause the bellows to apply the force to the first plate towards the second plate upon inflation and when the door assembly is in the closed position, wherein the force causes the first and second plates to apply a pressure to seal a cassette membrane to the peritoneal dialysis cassette and define one or more fluid flow paths within the peritoneal dialysis cassette.

17. The method of claim 16, further comprising locking, via an actuator, the latch assembly in a latched position upon inflating the bellows with the door assembly in the closed position.

* * * * *